(12) United States Patent
Sanderson et al.

(10) Patent No.: US 10,350,380 B2
(45) Date of Patent: Jul. 16, 2019

(54) SYSTEMS AND METHODS FOR DISTAL CONTROL OF HEALTH EFFECTORS

(71) Applicant: Soniphi LLC, Incline Village, NV (US)

(72) Inventors: Matthew Sanderson, Incline Village, NV (US); Mark Hinds, Incline Village, NV (US)

(73) Assignee: SONIPHI LLC, Incline Village, NV (US)

( * ) Notice: Subject to any disclaimer, the term of this patent is extended or adjusted under 35 U.S.C. 154(b) by 299 days.

(21) Appl. No.: 14/973,413

(22) Filed: Dec. 17, 2015

(65) Prior Publication Data

US 2017/0173295 A1    Jun. 22, 2017

(51) Int. Cl.
| | |
|---|---|
| *A61M 21/00* | (2006.01) |
| *A61B 7/04* | (2006.01) |
| *A61B 5/00* | (2006.01) |
| *A61B 5/024* | (2006.01) |

(52) U.S. Cl.
CPC .......... *A61M 21/00* (2013.01); *A61B 5/0051* (2013.01); *A61B 5/024* (2013.01); *A61B 7/04* (2013.01); *A61B 2562/0204* (2013.01); *A61M 2021/0027* (2013.01); *A61M 2021/0055* (2013.01); *A61M 2021/0072* (2013.01); *A61M 2205/3375* (2013.01)

(58) Field of Classification Search
CPC .............................................. A61M 21/00–02
See application file for complete search history.

(56) References Cited

U.S. PATENT DOCUMENTS

| | | |
|---|---|---|
| 7,195,780 B2 | 3/2007 | Dennis et al. |
| 8,380,296 B2 | 2/2013 | Lee et al. |
| 8,568,357 B2 | 10/2013 | Ortega et al. |
| 8,657,756 B2 | 2/2014 | Stahmann et al. |

(Continued)

FOREIGN PATENT DOCUMENTS

| | | |
|---|---|---|
| WO | 2012/048302 A2 | 4/2012 |
| WO | 2012048302 | 4/2012 |
| WO | 2015/069949 A1 | 5/2015 |

OTHER PUBLICATIONS

Eswaran, U. et al., "Embedded System Based Automated Drug Delivery Unit and MicroFluidics for drug discovery", International Journal of advanced Research in Computer and Communication Engineering, vol. 1, No. 1, Mar. 2012.

(Continued)

*Primary Examiner* — Thaddeus B Cox
(74) *Attorney, Agent, or Firm* — Fish IP Law, LLP

(57) ABSTRACT

A system for improving a health status of a person by analyzing and applying frequency information at a person is disclosed. The frequency information could be collected from an audio sample, or could be collected via feedback frequencies occurring when a test frequency is applied at the person. The system analyzes the collected frequency information to determine a status of the patient, for example a fundamental frequency of the person and/or a weak frequency of the person. Based upon the frequency information, the system generates a protocol to implement one or more frequencies at the person, for example sonic frequencies, light frequencies, and/or vibrational frequencies. Depending upon which frequencies are implemented, the state of the person can be improved.

34 Claims, 3 Drawing Sheets

(56) References Cited

U.S. PATENT DOCUMENTS

| | | | |
|---|---|---|---|
| 8,663,106 B2 | 3/2014 | Stivoric et al. | |
| 8,932,218 B1* | 1/2015 | Thompson | A61B 5/7235 600/300 |
| 9,055,917 B2 | 6/2015 | Mann et al. | |
| 2005/0107838 A1 | 5/2005 | Lovett et al. | |
| 2009/0099474 A1 | 4/2009 | Pineda et al. | |
| 2009/0143654 A1* | 6/2009 | Funane | A61B 5/14553 600/309 |
| 2010/0121170 A1 | 5/2010 | Rule | |
| 2011/0137110 A1* | 6/2011 | Aarts | A61M 21/02 600/27 |
| 2012/0296176 A1 | 11/2012 | Herbst | |
| 2014/0066844 A1 | 3/2014 | Rule | |
| 2014/0142645 A1* | 5/2014 | Weisbart | A61N 2/00 607/2 |
| 2014/0350401 A1 | 11/2014 | Sinelnikov | |
| 2015/0297108 A1 | 10/2015 | Chase et al. | |
| 2017/0106202 A1* | 4/2017 | Butinar | A61N 2/006 |
| 2017/0133035 A1* | 5/2017 | Jeon | H04R 1/10 |
| 2017/0312476 A1* | 11/2017 | Woo | A61M 21/02 |
| 2017/0316174 A1* | 11/2017 | Wild | G06F 19/3431 |

OTHER PUBLICATIONS

Murray, M.D., "Making Health Care Safer: A Critical Analysis of Patient Safety Practices—Chapter 11. Automated Medication Dispensing Device", AHRQ Publication, Jul. 20, 2001.
PCT Search Report dated Mar. 15, 2017 for PCT/US2016/067332 filed on Dec. 16, 2016 entitled Systems and Methods for Distal Control of Health Effectors.

\* cited by examiner

SYSTEMS AND METHODS FOR DISTAL CONTROL OF HEALTH EFFECTORS

FIELD OF THE INVENTION

The field of the invention is distal health treatment devices.

BACKGROUND

The background description includes information that may be useful in understanding the present invention. It is not an admission that any of the information provided herein is prior art or relevant to the presently claimed invention, or that any publication specifically or implicitly referenced is prior art.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

People frequently need to have medical needs diagnosed from a distal location, but are either unable or unwilling to travel to a doctor in order to have the medical needs diagnosed. In such situations, a medical doctor needs to travel to the sick person in order to diagnose the person. However, hiring a medical doctor to travel to the bedside of a sick patient is not always feasible or cost-effective, and, unless the doctor is a specialist, the doctor frequently cannot provide adequate bedside care.

U.S. Pat. No. 8,380,296 to Lee teaches an implantable medical device that uses brain state information to activate, de-activate, and/or modify therapy for a patient. The medical device can detect a seizure and can activate an implanted defibrillator to steady the heart of the patient, or even restart the heart of a patient having heart problems. However, many patients either cannot afford, or do not want, a medical device implanted within their body. In addition, Lee's implantable medical device can only diagnose a small number of heart-related illnesses.

U.S. Pat. No. 8,657,756 to Stahmann teaches a system with an implantable internal sensors that sends movement data to an external processing system. A diagnosis processor could then diagnose a disease or disorder based upon the sensor information, which could then be sent to a therapy device, such as a drug delivery device or a nerve stimulation therapy device. Stahmann's system, however, requires a device to be implanted into the system for detailed analysis. Again, many patients either cannot afford, or do not want, a medical device implanted within their body.

U.S. Pat. No. 8,663,106 to Stivoric teaches a system that measures the temperature of a human body non-invasively using skin and ambient temperature sensors. The system can derive and predict a number of physiological and conditional states and events, and a caregiver could program devices that detect certain use-related conditions to deliver medication or other nutrients in response. Stivoric, however, can only predict a limited number of conditions by monitoring the temperature of the patient, and many patients prefer not to ingest medication in response to a detected malady.

Thus, there remains a need for a system and method to improve the detection and treatment of various medical conditions.

SUMMARY OF THE INVENTION

The following description includes information that may be useful in understanding the present invention. It is not an admission that any of the information provided herein is prior art or relevant to the presently claimed invention, or that any publication specifically or implicitly referenced is prior art.

The inventive subject matter provides apparatus, systems, and methods in which a diagnosis system uses frequencies to improve the health status of the person. The system could use any suitable frequency information to derive the health of the person, for example bio-acoustic information, bio-electronic information (e.g. electromagnetic frequencies, heart-rate frequencies, galvantic skin response frequencies), bio-magnetic information, bio-vibrational information, and bio-luminescent information (light frequencies). As used herein, "bio-acoustic information" comprises sonic information embedded within a voice sample—excluding linguistic data. As used herein, "linguistic data" comprises any information that requires knowledge of a language to decipher and/or understand, such as English, Russian, or Mandarin Chinese. As used herein, "bio-electronic information" comprises electronic impulses, such as current, voltage, and frequency, emanating from a person. As used herein, "bio-magnetic information" comprises any magnetic fields detected from a person. As used herein, "bio-vibrational information" comprises any tactile vibrations detected upon a surface of a person or upon a surface of clothing worn by the person. As used herein, "bio-luminescent information" comprises light waves reflecting off of a surface of the person. Preferably, the system uses the frequency information to develop a protocol that implements a frequency for a duration of time at the person. As used herein, "at the person" means within two meter's distance from a center of the person, and more preferably within 1.5 meter's distance from a center of the person, within 1 meter's distance from a center of the person, or even within 0.5 meter's distance from the center of the person. Devices located "at the person" could be worn by the person, be placed within a pocket worn by the person, could be embedded within a body part of the person, or could be placed within a proximate area of the person.

The system can collect frequency information from the person in a variety of ways. In some embodiments, the system collects passive emitted frequency data, such as bio-acoustic information via a person speaking into a microphone or heart rate information via a person wearing an electro dermal device. In systems that collect bio-acoustic information, the system could record a voice sample that contains bio-acoustic information emitted by the person's voice. In other embodiments the system emits frequencies at the person, such as a laser aimed at portions of the person's body at a frequency or an electrode that transmits electronic signals through the person's body, and detects frequency feedback from the person's body similar to a radar "pinging" portions of the person's body. In systems that collect bio-electronic information, the system could record electronic impulses detected through an electrodermal sensor. In some embodiments, the system implements a frequency sweep of a part of the person's body to derive the strength of resonant frequencies.

Frequency information could be collected by a sensor at the person, for example a microphone embedded in a cellular phone or an electronic wearable device functionally coupled to a computer system, which transmits frequencies to the computer system. In some embodiments, the sensor could be surgically implanted within the person's body, such as within a pacemaker or other implantable device, which transmits detected frequencies to a computer system functionally coupled to the sensor. As used herein, an electronic device that is "functionally coupled" to another electronic device is coupled in such a way as to allow electronic data to be transmitted from one electronic device to another electronic device, using a wired or wireless data connection. Contemplated sensors include microphones, electroencephalograms, electrodermal sensors, cameras, infrared sensors, and antennas. The frequency information could be a sample over any period of time suitable to collect enough information to derive a person's state, for example at most 2 seconds, at most 5 seconds, at most 10 seconds, at most 30 seconds, at most 1 minute, or even at most 5 minutes. In some embodiments, a user interface might be presented to the person, triggering the person to perform an activity that would cause frequencies of the person to be easier to capture, such as placing electrodermal sensors on a portion of the person's body, or read a sentence presented on the user interface into a microphone sensor. The sensor could be configured to transmit either the raw data to a remote computer system, or could be configured to transmit only derived frequency information (e.g. bio-acoustic information, bio-electronic information, bio-magnetic information, bio-vibrational information, or bio-luminescent information) to a remote computer system distal from the person for processing.

Frequency information extracted from the collected raw sensor data is typically transmitted to a frequency processing module to be analyzed. In preferred embodiments, the frequency information is analyzed by a computerized frequency processing module which derives frequency information from the collected raw data from the sensor or sensors at the person. Preferably, a full spectral analysis of the raw data is performed in order to extract as much frequency information as possible from the raw data. Exemplary frequency information includes, for example, a highest dB (decibel) reading, a lowest dB reading, cumulative octave readings, harmonics, and logical groupings of frequencies. In some embodiments, the frequency processing module could be configured to derive a fundamental frequency from the raw data. As used herein, a "fundamental frequency" comprises the lowest frequency produced by the oscillation of an object. In some embodiments, the frequency processing module could derive the fundamental frequency to be the lowest frequency detected within the voice sample, and in other embodiments, the frequency processing module could derive the fundamental frequency to be the lowest frequency of a minimum threshold volume level, for example over 60 dB or over 40% of the loudest sound within the audio sample. In other embodiments, the frequency processing module could derive the fundamental frequency to be the strongest (e.g. highest decibel) frequency detected within a portion of the voice sample, or the strongest whole-number frequency detected within a portion of the voice sample.

In some embodiments, the frequency processing module could be configured to derive a disease state of the person. For example, the frequency processing module could be configured to detect whether a portion of the person's throat is injured by detecting which frequencies the person sings well vs. the frequencies the person sings poorly. (e.g. a person might sing a C note at a high decibel level but an F# note at a low decibel level or at an uneven, scratchy decibel) In other embodiments, the frequency processing module could be configured to detect a strength of the person's fundamental frequency. In such embodiments, the frequency processing module could detect weak or unsteady frequencies in the received frequency information.

The system preferably uses the frequency information to develop a protocol that implements a frequency at a corresponding duration. Typically the frequency information is fed into a treatment module that develops the protocol as a function of a portion of the frequency information. As used herein, a protocol that "implements" a frequency at a duration is one that instructs a device to resonate at the frequency for the duration specified. A protocol could be configured to implement a plurality of frequencies at a plurality of durations if need be. Such frequencies could be implemented using any suitable device that could be directed to resonate at a frequency, for example an audio speaker, a laser, a light source, a pulsed electromagnetic field (PEMF) device, a SCALAR wave device, a transcutaneous electrical nerve stimulation (TENS) device, a microcurrent electrical nerve stimulation (MENS) device, or a vibrational motor that transmits a tactilely sensible vibrational frequency. In some embodiments, the system could construct a protocol to implement a weakly detected frequency in the bio-acoustic information. In simple embodiments, the system could construct a protocol to implement the fundamental frequency for the period of time that the voice sample was recorded. The system could also construct a protocol to implement a harmonic of the fundamental frequency, multiple harmonics of the fundamental frequency, or could implement the fundamental frequency via different modalities (e.g. via an audio sound and also a visual light). In some embodiments, the protocol could implement the frequency by aiming the frequency at a portion of the person's body, for example the person's ears, eyes, nose, throat, chest, or hips. In other embodiments, the protocol could implement the frequency by aiming the frequency at multiple portions of the person's body, and could implement different frequencies at different portions of the person's body (e.g. directing the fundamental frequency towards the person's ears, and a harmonic of the fundamental frequency towards the person's diaphragm). Where a plurality of frequencies are directed at a person, each frequency could be implemented at a different duration and/or duty cycle.

The system could receive several sets of frequency information from a person, for example through several samples of data collected from the sensors one after another (e.g. within 5 minutes of one another) or through several historical samples of data submitted over time and saved to an archived database (e.g. one week, one month, or even one year after one another). Several protocols could be developed, one for each set of frequency information, and/or each type of frequency information. In some embodiments, the system could be configured to compare a first set of frequency information with a second set of frequency information in order to develop a follow-up protocol. For example, where the system is configured to strengthen a fundamental frequency of a person, the system could detect a decibel level of the person's fundamental frequency in accordance with the first set of frequency information, and the decibel level of the person's fundamental frequency in accordance with the second set of frequency information, and could increase/decrease the intensity of the implemented frequency depending upon if the fundamental frequency decreased/increased in decibel level, respectively. In some embodiments, the system could be configured to save the received frequency information to a database to provide a historical frequency map of the person. Such historical frequency maps could be used to develop person-specific protocols.

For example, the system could determine that the person regains an intensity in voice samples or frequency feedback when a first frequency is implemented at the person, but fails to regain an intensity (or does not gain as large an intensity) when a second frequency is implemented at the person. The system could then favor implementing the first frequency at the person when such an analysis is performed. In some embodiments, the system could save the raw frequency information into the database, but preferably the system only saves historical analysis information to the database to save space. Exemplary analysis information includes a fundamental frequency of the person, a set of harmonic frequencies that are known to strengthen the fundamental frequency of the person, the highest recorded decibel frequency, the lowest recorded frequency, the types of frequency recorded and implemented at the person, and a preferred fundamental frequency of the person. The system could save the frequency information in a variety of ways, for example by molecular weight and frequency correlations, by genetic code and wavelength correlations, and/or as light emission spectral analysis data.

Once one or more protocols have been developed by the treatment module, the system could transmit the protocol to a computerized control module that implements the frequency for the corresponding duration at the person. Contemplated control modules include cellular telephones and other wearable or mountable computer systems functionally coupled to one or more effectors, or implantable devices that are functionally coupled to one or more effectors. As used herein, an "effector" comprises a device that can implement a frequency, such as an audio speaker, a light source (e.g. an LED or laser), a vibrational source, a PEMF device, and a SCALAR wave device. The control module could then implement the protocol at the person in order to affect the health of the person, for example by a frequency by implementing the frequency and/or a harmonic of the frequency, or by cancelling or decreasing frequencies that are higher than a threshold value through frequency-cancelling systems (e.g. noise-cancelling systems). Thus, the control module follows the instructions of the protocol and implements at least one frequency for a specified duration once a protocol has been received. In some embodiments, the control module could perform a frequency sweep of the person to ensure that the treatment is effective. For example, the control module could activate electrodes coupled to a skin of the person, or embedded within the person, which will sweep through a specified range of frequencies and test for harmonic resonance via conductance/HRV/GSR. The control module could be configured to test for resonance among different types of frequencies, for example a bio-electric frequency analysis in response to an acoustic frequency applied at the person. The control module could monitor the person's body's response to determine resonance, and could allow a monitoring device to generate even more precise frequency sets and series for treatment over time. In some embodiments, the system could be configured to implement the frequency upon a group of people, and detect frequency feedback reverberating from the people.

Various objects, features, aspects and advantages of the inventive subject matter will become more apparent from the following detailed description of preferred embodiments, along with the accompanying drawing figures in which like numerals represent like components. For example, instead of implementing frequencies at the person, the system could be configured to implement the frequency into food or water, which could then be ingested by the person. In other embodiments, the system could be configured to implement the frequency into an ingestible medium or into a wearable medium (e.g. a quartz crystal), which is then transported to the person for wearing.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

DETAILED DESCRIPTION

Figure 1:
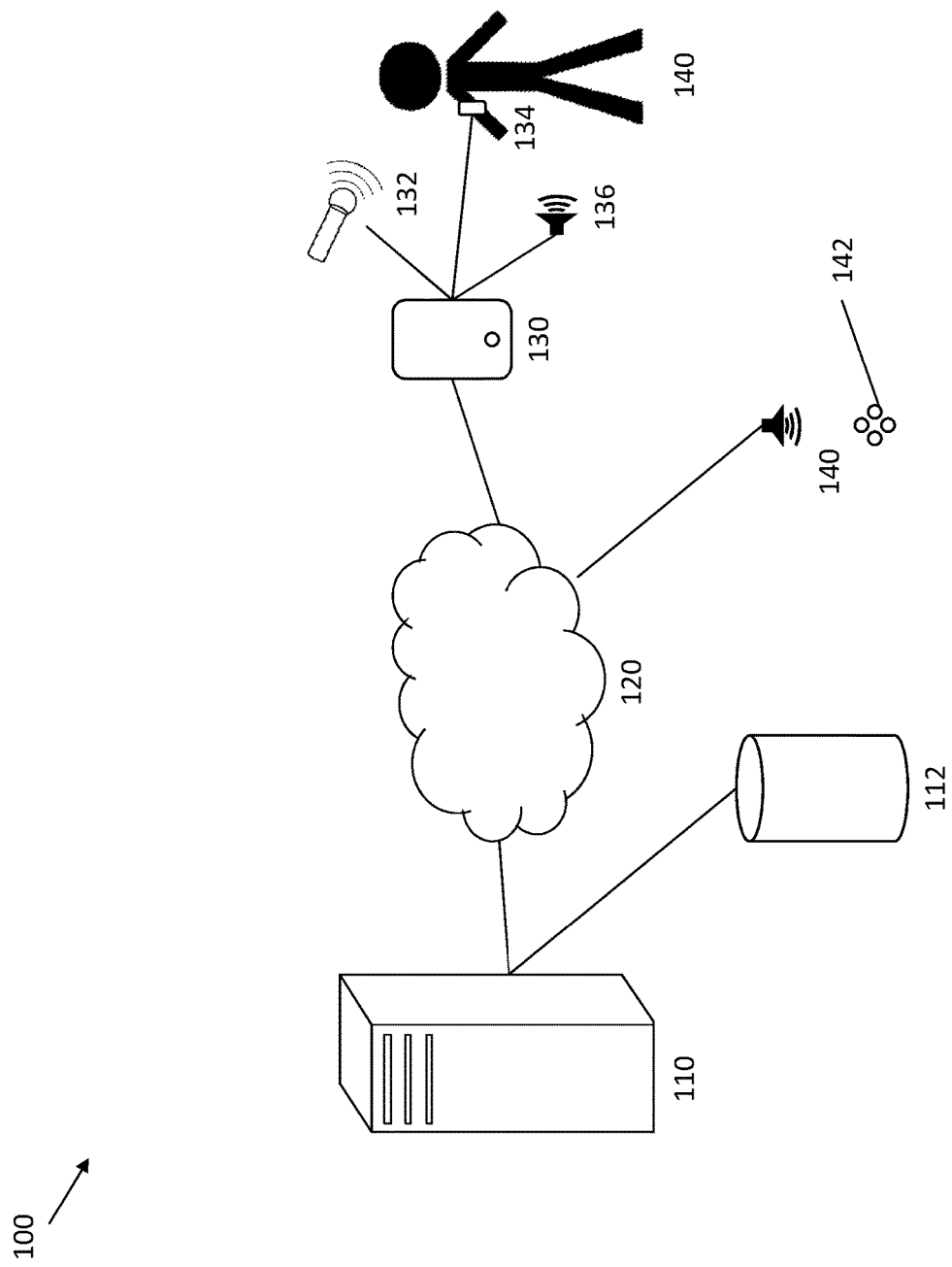
FIG. 1 is an exemplary system distributed on a computer system and a portable device at the person

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be noted that any language directed to a computer system should be read to include any suitable combination of computing devices, including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

One should appreciate that the disclosed techniques provide many advantageous technical effects including the ability to detect, and improve, the health status of a person via frequency analysis.

The inventive subject matter provides apparatus, systems, and methods to detect, and improve, the health status of a person via bio-acoustic information.

In FIG. 1, a system 100 includes an analysis computer system 110, a network 120, a control computer system 130, and a person 140.

Analysis computer system 110 is shown euphemistically as a single computer tower having a processor and a non-transient memory with software configured to perform analysis and protocol development on a voice sample or a set of frequency information, but analysis computer system 110 could be distributed among a plurality of computers, or could be implemented on a network cloud without departing from the scope of the current invention. Data source 112 is functionally coupled to computer system 110 and stores data collected and/or analyzed by analysis computer system 110, such as frequency data, health status reports, profile data, and/or preferences. Such data sources typically store collected information in a text file, such as a log, csv, JSON or an XML file. Data source 112 could be a DBMS, such as SQL® or Oracle®, which keeps data in a structured environment, and typically keeps metadata log files on its datasets. While data source 112 is shown euphemistically as a single data repository, any number of data sources and any type of data source could be used without departing from the scope of the invention. The data sources coupled to computer 110 could number in the hundreds or even thousands, to provide a large corpus of datasets that may or may not be known to computer system 110, where many of the data sources might use different types of data structures.

Analysis computer system 110 is functionally coupled to frequency data collectors 132 and 134 in a manner such that analysis computer system 110 could receive or retrieve frequency datasets from frequency data collector 132. While analysis computer system 110 could be physically coupled to control computer system 130, analysis computer system 110 is preferably functionally coupled to each data source through a network link 120, such as an intranet or the Internet. Network 120 is shown euphemistically has a cloud of computer systems functionally coupled with one another, such as an intranet or the Internet, but could be any data connection between analysis computer system 110 and control computer system 130. Analysis computer system 110 is configured to retrieve datasets from one or more control computer systems 130, and consolidate the retrieved datasets into one or more new datasets, which are saved in data repository 112—a non-transitory computer readable medium functionally coupled to analysis computer system 110. Data repository 112 could also be considered a data source having one or more datasets that analysis computer system 110 could draw upon. Data repository 112 could also contain a historical log that tracks all retrieving, profiling, querying and conforming of datasets, attributes of datasets, and associated user entity interactions to enable the system to learn from itself by analyzing trends found in the historical log.

Typically, data source 112 stores data collected from remote sensors, such as frequency data collectors 132 and 134 coupled to control computer system 130, which is functionally coupled to analysis computer system 110 via network 120. Control computer system 130 is shown as a mobile telephone, but could be a wearable computer device (e.g. a badge, a pin, a button, a cufflink, a watch, a bracelet, a necklace, an elbow pad, or a piece of clothing), an implantable device, or could be coupled to a portion of a skin of person 140, such as a bracelet, a belt, or an electrodermal heart rate monitor. In some embodiments, control computer system 130 is distributed about the body of person 140, such as a mobile computer system and several Bluetooth-connected devices configured to transmit frequencies at person 140. Here, control system 130 has frequency data collectors 132 and 134, and an effector 134. While frequency data collector 132 is shown euphemistically as a single microphone, and frequency data collector 134 is shown euphemistically as a single electrodermal patch coupled to an arm of person 140, frequency data collectors 132 and 134 could comprise one or more sensors that receive frequency datasets from person 140, for example an electrodermal sensor, electroencephalogram, camera, infrared sensor, or antenna. As used herein, a "frequency dataset" is a dataset that contains oscillating wave data collected by a sensor. One or more sensors could be implanted within person 140, but is preferably wearable, placed in a pocket, or is coupled to a portion of person 140's skin, such as a bracelet or a belt. Frequency data collectors 132 and/or 134 could comprise a plurality of sensors that collectively communicate frequency data sets to computer system 130. In some embodiments, frequency data collectors 132 and 134 collect frequency data passively, for example by instructing person 140 to provide a voice sample, but in preferred embodiments frequency data collectors 132 and 134 collect frequency feedback data resonating from person 140 in response to frequencies implemented by effector 136.

Effector 136 is shown euphemistically as a single audio speaker, but could be any combination of suitable devices that transmit frequency information at person 140, for example a laser, a light source, a pulsed electromagnetic field (PEMF) device, a SCALAR wave device, a transcutaneous electrical nerve stimulation (TENS) device, a microcurrent electrical nerve stimulation (MENS) device, or a vibrational motor that transmits a tactilely sensible vibrational frequency. Control system 130 transmits a protocol to effector 136 to transmit a frequency to person 140, and remote computer system 130 then collects frequency datasets via frequency data collectors 132 and 134 and transmits at least a portion of the datasets to analysis computer system 110 for analysis. In some embodiments, remote computer system 130 could transform the raw collected frequency datasets, for example by gleaning only bioacoustic data from a voice sample and transmitting only the bioacoustic data to analysis computer system 110, however in other embodiments remote computer system 130 could be configured to transmit raw frequency datasets to analysis computer system 110.

Analysis computer system 110 could also be configured to derive frequency information extracted from the frequency sample. In preferred embodiments, the frequency information is analyzed by a computerized frequency processing module which derives frequency information from the frequency dataset(s). Preferably, a full spectral analysis of the frequency dataset(s) is performed in order to extract as much non-linguistic frequency information as possible. Exemplary frequency information includes, for example, a highest dB (decibel) reading, a lowest dB reading, cumulative octave readings, harmonics, and logical groupings of frequencies. In some embodiments, the frequency processing module could be configured to derive a fundamental frequency within the frequency feedback sample. As used herein, a "fundamental frequency" comprises the lowest frequency produced by the oscillation of an object. In some embodiments, the frequency processing module could derive the fundamental frequency to be the lowest frequency detected within the frequency dataset(s), and in other embodiments, the frequency processing module could derive the fundamental frequency to be the lowest frequency of a minimum threshold volume level, for example over 60 dB or over 40% of the loudest sound within the audio sample. In other embodiments, the frequency processing module could derive the fundamental frequency to be the strongest frequency detected within a portion of the frequency feedback sample, or the strongest whole-number frequency detected within a portion of the frequency feedback sample.

In some embodiments, the frequency processing module could be configured to diagnose a disease state of the person. For example, the frequency processing module could be configured to detect whether a portion of the person's throat is injured by detecting which frequencies the person sings well vs. the frequencies the person sings poorly. (e.g. a person might sing a C note at a high decibel level but an F# note at a low decibel level or at an uneven, scratchy decibel) In such embodiments, the frequency processing module could detect weak or unsteady frequencies in the frequency dataset(s) and implement a protocol to strengthen the weak or unsteady frequencies. For example, a person could sing a range of notes, and analysis computer system 110 could select an octave of notes (e.g. the mean, median, or average octave) and detect that the person's C note and D note is less than a threshold level (e.g. 30% weaker) than the average decibel level for the selected octave of notes, while the person's A note is more than a threshold level (e.g. 30% stronger) than the average decibel level for the selected octave of notes.

The frequency information is then preferably used to develop a protocol that implements a frequency at a corresponding duration. Typically the frequency information is fed into a treatment module that develops the protocol as a function of a portion of the frequency information. As used herein, a protocol that "implements" a frequency at a duration is one that instructs a device to resonate at the frequency for the duration specified. A protocol could implement a plurality of frequencies at a plurality of durations if need be. Such frequencies could be implemented using any suitable device that could be directed to resonate at a frequency, for example an audio speaker, a laser, a light source, a pulsed electromagnetic field (PEMF) device, a SCALAR wave frequency, or a vibrational motor that transmits a tactilely sensible vibrational frequency. In some embodiments, the system could construct a protocol to implement a weakly detected frequency in the frequency information. In simple embodiments, the system could construct a protocol to implement the fundamental frequency for the period of time that the frequency feedback sample was recorded. The system could also construct a protocol to implement a harmonic of the fundamental frequency, multiple harmonics of the fundamental frequency, or could implement the fundamental frequency via different modalities (e.g. via an audio sound and also a visual light). In some embodiments, the protocol could implement the frequency by aiming the frequency at a portion of the person's body, for example the person's ears, eyes, nose, throat, chest, or hips. In other embodiments, the protocol could implement the frequency by aiming the frequency at multiple portions of the person's body, and could implement different frequencies at different portions of the person's body (e.g. directing the fundamental frequency towards the person's ears, and a harmonic of the fundamental frequency towards the person's diaphragm). Where a plurality of frequencies are directed at a person, each frequency could be implemented at a different duration, phase, and/or duty cycle.

In some embodiments, analysis computer system 110 could be configured to transmit the frequency protocol to frequency infuser 140, which is shown here as a speaker that implements frequencies to frequency medium 142. Frequency infuser 140 is shown euphemistically as a speaker, but could be any suitable effector. Frequency medium 142 is shown euphemistically as a set of pills that could then be sent to person 140 to be ingested, but could be any sort of medium that absorbs frequencies from an effector, such as a crystal (e.g. quartz or amethyst) that could be worn or a bracelet.

Figure 2:
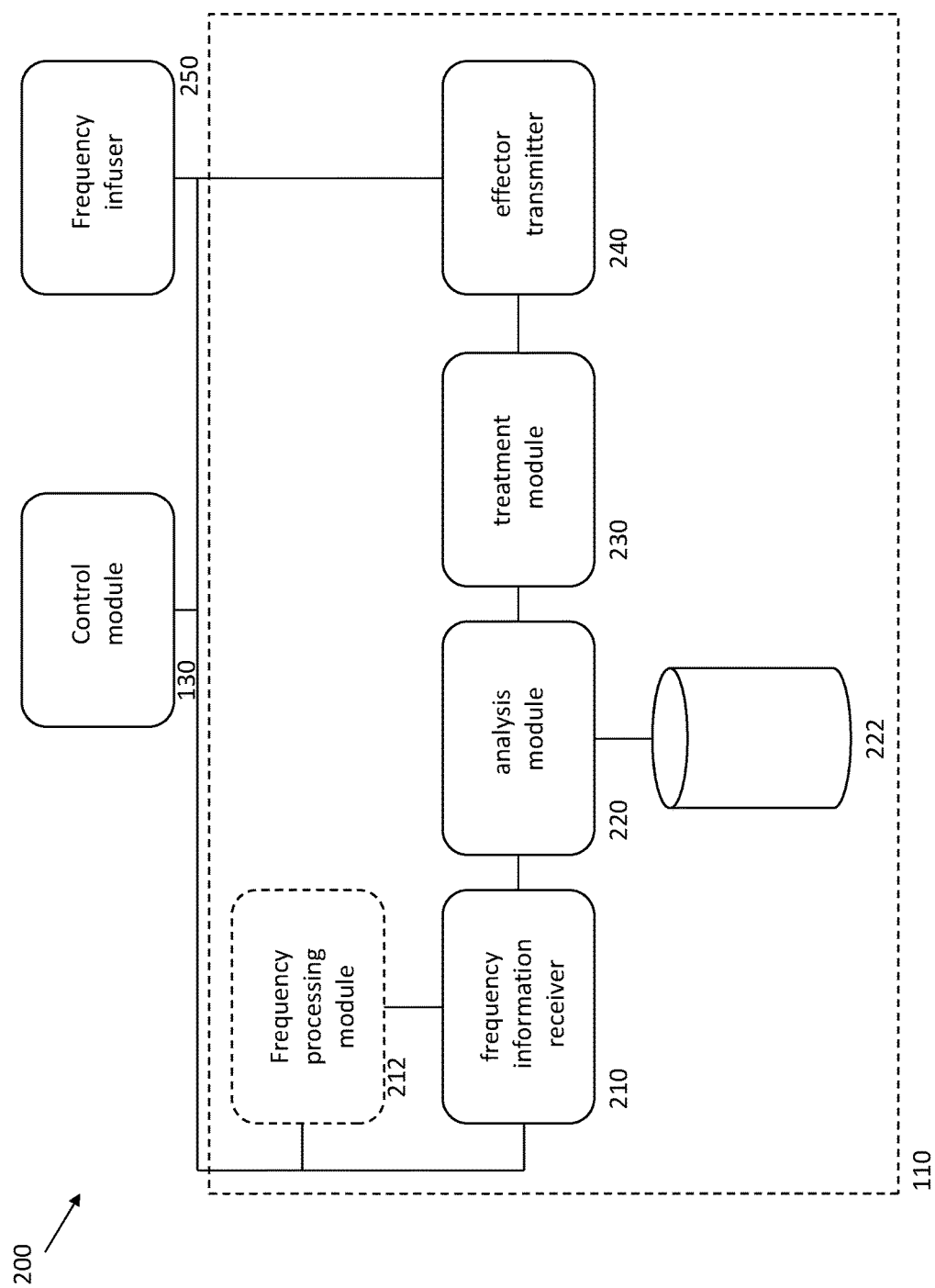
FIG. 2 is a software schematic of the computer system and portable device of FIG. 1.

FIG. 2 shows a software schematic of modules within analysis computer system 110, having an frequency information receiver 210, an analysis module 220, a treatment module 230, an effector transmitter 240, and an optional frequency processing module 212.

Frequency information receiver 210 is a software module that is configured to collect any number of frequency datasets from any number of data sources coupled to analysis computer system 110. Frequency information receiver 210 could be configured to process frequency datasets collected from a user entity through an interface module (not shown, for example from a user interface (not shown) or from a calling computer system (not shown). In some embodiments, the user might request analysis computer system 110 to analyze received frequency dataset information, while in other embodiments analysis computer system 110 could automatically instruct a remote control computer system to poll frequency dataset information from the person (preferably feedback frequency dataset information) in accordance with a schedule. In some embodiments, raw frequency datasets are first processed by frequency processing module 212 to analyze only the frequency information from a received dataset (e.g. analyzing only the bioacoustic information contained within a voice sample).

Analysis module 220 could be configured to analyze the received frequency dataset information as a function of the corpus of datasets in database 222 and derive and determine potential relationships between attributes. Frequency information receiver 210 could receive several sets of frequency information from a person, for example through several samples of data collected from the sensors one after another (e.g. within 5 minutes of one another) or through several historical samples of data submitted over time and saved to an archived database (e.g. one week, one month, or even one year after one another). Analysis module 220 could then compare the received frequency dataset information against historical frequency dataset information from the person, or from other persons with similar characteristics. The similar characteristics could be selected through an administrator user interface. For example, a user could wish to compare the frequency feedback dataset against frequency characteristics of other users who have the same racial background, the same age and sex, and/or the same profession. In some embodiments, a user could compare his/her own frequency feedback information against a selected ideal frequency dataset.

The treatment module 230 then generally develops a protocol as a function of the comparison of the received frequency dataset information against the saved frequency dataset information in database 222. Several protocols could be developed, one for each set of frequency information, and/or each type of frequency information. In some embodiments, treatment module 230 could be configured to compare a first set of frequency information with a second set of frequency information in order to develop a follow-up protocol. For example, where treatment module 230 is configured to strengthen a fundamental frequency of a person, treatment module 230 could detect a decibel level of the person's fundamental frequency in accordance with the first set of frequency information, and the decibel level of the person's fundamental frequency in accordance with the second set of frequency information, and could increase/decrease the intensity of the implemented frequency depending upon if the fundamental frequency decreased/increased in decibel level, respectively. In some embodiments, treatment module 230 could be configured to save the received frequency information to a database to provide a historical frequency map of the person. Such historical frequency maps could be used to develop person-specific protocols. In other embodiments, treatment module 230 might seek to adjust the person's frequency information to closely mirror a previously selected "idealized frequency map," strengthening certain frequencies and cancelling other frequencies such that the person's feedback more closely resembles the idealized frequency map previously selected (e.g. by the person through a user interface on the control computer system or by an administrator "trainer").

In other embodiments, treatment module 230 could determine that the person regains an intensity in voice samples or frequency feedback when a first frequency is implemented at the person, but fails to regain an intensity (or does not gain as large an intensity) when a second frequency is implemented at the person. Treatment module 230 could then favor implementing the first frequency at the person when such an analysis is performed. In some embodiments, treatment module 230 could save the raw frequency information into the database 222, but preferably the system only saves historical analysis information to the database 222 to save space. Exemplary analysis information includes a fundamental frequency of the person, a set of harmonic frequencies that are known to strengthen the fundamental frequency of the person, the highest recorded decibel frequency, the lowest recorded frequency, the types of frequency recorded and implemented at the person, and a preferred fundamental frequency of the person. Treatment module 230 could save the frequency information in a variety of ways, for example by molecular weight and frequency correlations, by genetic code and wavelength correlations, and/or as light emission spectral analysis data.

In some embodiments, the protocol could implement a frequency at different modalities. For example, two frequencies could be directed at a portion of the person's body/tissue (e.g. the person's diaphragm, head, or wrist) via electrodes. A positive electrode and a negative electrode could transmit a frequency that crosses to create a targeted location of wave interference. The wave interference could be the fundamental frequency the protocol is designed to strengthen or could cancel a frequency that the protocol is designed to weaken (e.g. above a predetermined threshold decibel level). In this manner, portions within the body of the person could be targeted to receive frequency information via the protocol without needing to implant an effector within the person's targeted organ.

Once one or more protocols have been developed, one or more protocols could then be sent to control module 130 by effector transmitter 240. Effector transmitter 240 transmits one or more protocols to the control module for implementing frequencies at the person, possibly sequentially or in parallel with one another. In some embodiments, the protocols are transmitted to cause resonance with one another. Preferably, control module collects feedback frequency datasets while the protocol is being implemented, so that analysis module 220 could ensure that the effector frequencies are being properly implemented at the person.

In some embodiments, effector transmitter 240 could transmit the protocol to a frequency infuser 250, which is coupled to a system that infuses a frequency medium with the transmitted frequency. In this manner, the treatment could be performed upon a frequency medium, which then is sent to the person who is analyzed. In other embodiments, an idealized set of frequency data selected by a user of control module 130 could be analyzed by analysis module 220, and the fundamental frequency of that person could then be sent to frequency infuser 250 to infuse a medium, such as a pill or a crystal to be sent to the person. In this manner, the person can ingest a medium infused with the fundamental frequency of an idealized set of frequency data (e.g. from the person's hero), or can wear a crystal imbued with the frequency information.

Figure 3:
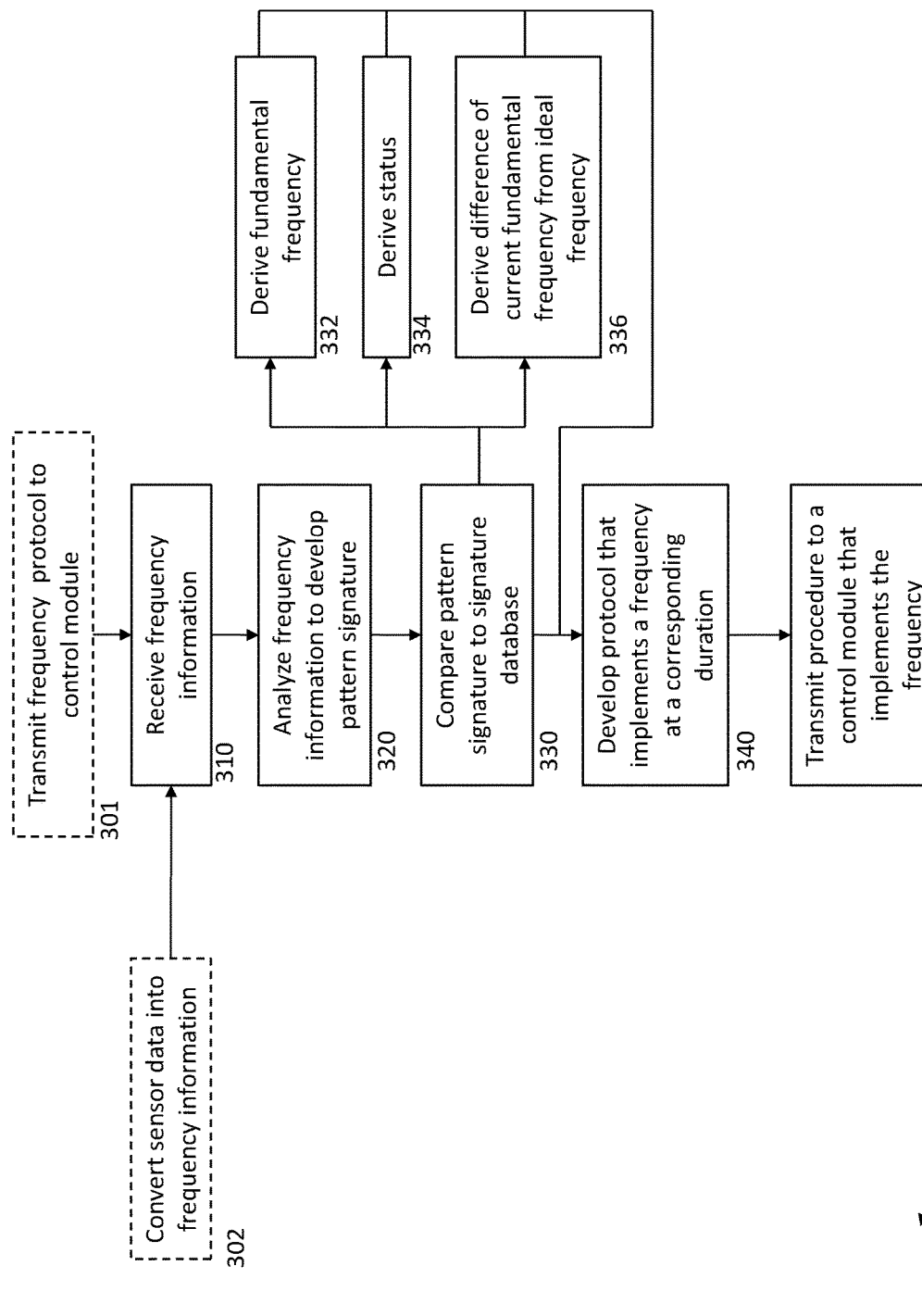
FIG. 3 is a flowchart of steps to affect the health of the person in response to received bio-acoustic information.

In FIG. 3 an exemplary series of steps 300 shows steps that could be performed in order to improve the health of a person. In optional step 301, the system transmits a frequency protocol to a control module to ensure that frequency feedback information is collected by frequency data collectors at the person. In optional step 302, a system could convert raw sensor data into frequency information. In other embodiments, the raw sensor data is simply sent as frequency information to the system in step 310. In either case, the system receives frequency information in step 310 (either raw or processed), and analyzes the frequency information in step 320 to develop a pattern signature of the received frequency dataset. The system then compares the pattern signature to a signature database of frequency information. Many different types of analysis' techniques could be applied during this comparison. For example, in step 332 the system could derive a fundamental frequency of the person, in step 334 the system could derive a physical status of the person, and/or in step 334 the system could derive a difference of the person's current fundamental frequency from an idealized fundamental frequency. Using this information, the system could develop a protocol that implements a frequency at a corresponding duration in step 340. The protocol could then transmitted to a control module in 350, which then implements the frequency at the person or to a frequency medium.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method for analyzing and improving a health status of a person, comprising:
    transmitting a first protocol to a control module that implements a first frequency at a first duration via at least one of an audio speaker, a light source, a vibrational source, or a Scalar wave device at the person;
    receiving a first set of frequency feedback information from the control module, wherein the frequency feedback information is derived from at least one of bio-acoustic information, bio-vibrational information, or bio-luminescent information;
    comparing a pattern signature in the frequency feedback information to a pattern signature in a database associated with the person;
    using a portion of the first set of frequency feedback information to derive a fundamental frequency of the person;
    wherein deriving the fundamental frequency comprises deriving the fundamental frequency as a strongest whole-number frequency detected within the portion of the first set of frequency feedback information;
    using the portion of the first set of frequency feedback information and the derived fundamental frequency to develop a second protocol that implements a second frequency and a corresponding second duration; and
    transmitting at least a portion of the second protocol to the control module to implement the second frequency via at least one of an audio speaker, a light source, a vibrational source, or a Scalar wave device at the corresponding second duration at the person.

2. The method of claim 1, further comprising a sensor, wherein the sensor comprises a cellular phone.

3. The method of claim 1, further comprising a sensor, wherein the sensor comprises a wearable device.

4. The method of claim 1, further comprising receiving, via the control module, a full spectral analysis of the first set of frequency feedback information.

5. The method of claim 1, wherein the portion of the first set of frequency feedback information comprises a highest dB reading.

6. The method of claim 1, wherein the portion of the first set of frequency feedback information comprises a lowest dB reading.

7. The method of claim 1, wherein the portion of the first set of frequency feedback information comprises cumulative octave readings.

8. The method of claim 1, wherein the portion of the first set of frequency feedback information comprises harmonic readings.

9. The method of claim 1, wherein the portion of the first set of frequency feedback information comprises frequency groupings.

10. The method of claim 1, wherein the step of using the portion of the first set of frequency feedback information to derive the fundamental frequency comprises deriving the fundamental frequency as a function of the first frequency and the corresponding first duration.

11. The method of claim 10, wherein the first frequency is the fundamental frequency.

12. The method of claim 10, wherein the first frequency is a harmonic of the fundamental frequency.

13. The method of claim 1, wherein the step of using the portion of the first set of frequency feedback information to derive the fundamental frequency comprises deriving the fundamental frequency as a strongest frequency detected within the portion of the first set of frequency feedback information.

14. The method of claim 1, wherein the step of using the portion of the first set of frequency feedback information to develop the second protocol that implements the second frequency and the corresponding second duration comprises deriving the second frequency as a resonance frequency of the person.

15. The method of claim 14, further comprising deriving a feedback frequency from the first set of feedback frequency information, wherein the step of using the portion of the first set of frequency feedback information to develop the second protocol that implements the second frequency and the corresponding second duration comprises deriving the second frequency as a frequency between the first frequency and the derived feedback frequency.

16. The method of claim 15, wherein the second frequency splits a difference between the first frequency and the derived feedback frequency.

17. The method of claim 1, further comprising, implementing, by the control module and in response to the first protocol, the first frequency via different modalities.

18. The method of claim 1, further comprising, implementing, by the control module and in response to the first protocol, the first frequency to target a first portion of the person's body.

19. The method of claim 1, further comprising, implementing, by the control module and in response to the first protocol, the first frequency to target multiple portions of the person's body.

20. The method of claim 1, further comprising using the portion of the first set of frequency feedback information to develop the second protocol to implement the second frequency and the corresponding second duration to target a second portion of the person's body.

21. The method of claim 1, further comprising, implementing, by the control module and in response to the first protocol, the first frequency at a corresponding duty cycle.

22. The method of claim 1, further comprising using, by the control module, the portion of the first set of frequency feedback information to diagnose a disease state of the person, wherein the first protocol is a function of the disease state.

23. The method of claim 1, wherein the step of using the portion of the first set of frequency feedback information to develop the second protocol comprises emitting the first frequency as a sonic frequency.

24. The method of claim 1, wherein the step of using the portion of the first set of frequency feedback information to develop the second protocol comprises emitting the first frequency as a light frequency.

25. The method of claim 1, wherein the step of using the portion of the first set of frequency feedback information to develop the second protocol comprises emitting the first frequency as a tactilely sensible vibrational frequency.

26. The method of claim 1, wherein the step of using the portion of the first set of frequency feedback information to develop the second protocol comprises emitting the first frequency as a pulsed electromagnetic field (PEMF) frequency.

27. The method of claim 1, wherein the step of using the portion of the first set of frequency feedback information to develop the second protocol comprises emitting the first frequency as a Scalar wave frequency.

28. The method of claim 1, further comprising:
receiving a second set of frequency feedback information from the control module;
using a portion of the second set of frequency feedback information to develop a third protocol that implements a third frequency and a corresponding third duration; and
transmitting at least a portion of the third protocol to the control module at the person that implements the third frequency at the corresponding third duration.

29. The method of claim 28, wherein the step of using the portion of the second set of frequency feedback information to develop the third protocol comprises comparing the portion of the second set of frequency feedback information against the portion of the first set of frequency feedback information to develop the second protocol.

30. The method of claim 28, further comprising saving the portion of the second set of frequency feedback information to the database to provide a historical frequency map of the person.

31. The method of claim 28, further comprising saving an analysis of the portion of the second set of frequency feedback information to the database to provide a historical frequency map of the person.

32. The method of claim 31, wherein the step of saving the analysis of the portion of the second set of frequency feedback information to the database comprises saving the analysis of the portion as molecular weight and frequency correlations.

33. The method of claim 31, wherein the step of saving the analysis of the portion of the second set of frequency feedback information to the database comprises saving the analysis of the portion as genetic code and wavelength correlations.

34. The method of claim 31, wherein the step of saving the analysis of the portion of the second set of frequency feedback information to the database comprises saving the analysis of the portion as light emission spectral analysis data.

* * * * *